(12) United States Patent
Moore (10) Patent No.: US 8,911,233 B2
(45) Date of Patent: Dec. 16, 2014

(54) DENTAL BUR STORAGE DEVICE

(75) Inventor: Paul Moore, County Galway (IE)

(73) Assignee: Gate Dental Services Limited, County Galway (IE)

( * ) Notice: Subject to any disclaimer, the term of this patent is extended or adjusted under 35 U.S.C. 154(b) by 119 days.

(21) Appl. No.: 13/504,568

(22) PCT Filed: Oct. 29, 2010

(86) PCT No.: PCT/EP2010/006617
§ 371 (c)(1),
(2), (4) Date: Jul. 9, 2012

(87) PCT Pub. No.: WO2011/050972
PCT Pub. Date: May 5, 2011

(65) Prior Publication Data
US 2012/0273446 A1 Nov. 1, 2012

(30) Foreign Application Priority Data
Oct. 29, 2009 (IE) .................................. S2009/0838

(51) Int. Cl.
*A61C 3/00* (2006.01)
*A61C 3/04* (2006.01)
*A61G 15/16* (2006.01)
*A47F 7/00* (2006.01)

(52) U.S. Cl.
CPC . *A61C 3/04* (2013.01); *A61G 15/16* (2013.01); *A47F 7/0028* (2013.01)
USPC ........................ 433/163; 211/70.6; 211/85.13

(58) Field of Classification Search
CPC ............ A61C 3/04; A61C 3/00; A61C 19/02; A61C 19/006; A61B 19/0256; A61B 19/26; A61B 19/0258; A61B 2019/0256; A61B 2019/0258; A61G 15/16; A61G 15/14; B25H 3/04; B25H 3/06; B25H 3/02; B25H 3/00; A47F 7/0028; A47F 7/0021; A47F 7/0035; A47F 7/02; B01L 9/06; B01L 9/54; B01L 9/00
USPC ...................... 211/85.13, 60.1, 70.6, 69, 69.1, 211/69.5–69.9; 433/77, 163; 206/368, 369, 206/370, 379, 63.5, 563, 362, 438, 443, 206/562, 564
See application file for complete search history.

(56) References Cited

U.S. PATENT DOCUMENTS

| | | |
|---|---|---|
| 1,357,041 A | 10/1920 | Fritch |
| 2,126,766 A * | 8/1938 | Gerbermann ................ 47/41.11 |

(Continued)

*Primary Examiner* — Jennifer E Novosad
(74) *Attorney, Agent, or Firm* — Tutunjian & Bitetto, P.C.

(57) ABSTRACT

The present invention is directed towards a dental bur storage device having a plurality of dental bur receiving holes capable of retaining a plurality of different dental bur types having different shank diameters, wherein, each of the plurality of dental bur receiving holes is tapered to allow a retaining fit to be established with any one of the plurality of different dental bur types having different shank diameters. The advantage of using a receiving hole that has a tapered form is that different types of dental burs having different diameters of shanks may be retained by the receiving holes in the dental bur storage device. This allows a wide range of different brands and different types of dental burs to be accommodated on one single dental bur storage device which greatly simplifies the process of selecting a dental bur for a dentist, particularly during a dental treatment. As the receiving hole is tapered, bur shanks of varying dimensions will be received to different depths within the receiving hole to a point where the receiving hole tapers to a diameter substantially equal to the diameter of the shank of the dental bur being received. Moreover, using this type of receiving hole, positive retention of a dental bur may be achieved when the dental bur storage device is handled roughly or inverted.

11 Claims, 8 Drawing Sheets

(56) References Cited

U.S. PATENT DOCUMENTS

| | | | |
|---|---|---|---|
| 3,270,416 A * | 9/1966 | Massa | 433/77 |
| 3,375,934 A * | 4/1968 | Bates | 211/72 |
| 3,643,812 A * | 2/1972 | Mander et al. | 211/74 |
| 4,121,719 A * | 10/1978 | Wilhelm | 211/69.5 |
| 4,253,830 A * | 3/1981 | Kazen et al. | 433/77 |
| 4,327,060 A * | 4/1982 | Nisii | 422/300 |
| 4,341,312 A * | 7/1982 | Scholer | 211/70.6 |
| 4,613,042 A * | 9/1986 | Aeschliman | 206/419 |
| 4,730,728 A * | 3/1988 | Larkin | 206/315.9 |
| 4,892,481 A * | 1/1990 | Kopunek et al. | 433/90 |
| 5,033,629 A * | 7/1991 | Caine | 211/69.5 |
| 5,190,169 A * | 3/1993 | Sincock | 211/60.1 |
| 5,289,919 A * | 3/1994 | Fischer | 206/571 |
| 5,356,383 A * | 10/1994 | Daly et al. | 604/110 |
| 5,823,363 A * | 10/1998 | Cassel | 211/60.1 |
| 5,975,295 A * | 11/1999 | Diamond | 206/366 |
| 5,993,745 A * | 11/1999 | Laska | 422/562 |
| 5,996,818 A * | 12/1999 | Boje et al. | 211/74 |
| 6,000,535 A * | 12/1999 | Berk et al. | 206/63.5 |
| 6,202,862 B1 * | 3/2001 | Acquaviva et al. | 211/69.5 |
| 6,257,539 B1 * | 7/2001 | Pelaez | 248/314 |
| 6,533,133 B2 * | 3/2003 | Liu | 211/74 |
| 6,640,981 B2 * | 11/2003 | Lafond et al. | 211/74 |
| D501,125 S * | 1/2005 | Winig et al. | D8/71 |
| 7,000,785 B2 * | 2/2006 | Jafari et al. | 211/74 |
| 7,036,668 B2 * | 5/2006 | Udy | 211/70.6 |
| 7,066,329 B2 * | 6/2006 | Riley | 206/443 |
| 7,264,117 B2 * | 9/2007 | Atkin et al. | 206/369 |
| 7,314,142 B2 * | 1/2008 | Lyman, Jr. | 211/69.5 |
| 7,331,450 B2 * | 2/2008 | Discko, Jr. | 206/63.5 |
| 8,002,547 B2 * | 8/2011 | Porter et al. | 433/173 |
| 8,162,138 B2 * | 4/2012 | Bettenhausen et al. | 206/339 |
| 8,348,067 B2 * | 1/2013 | Brown | 211/60.1 |
| 2002/0153336 A1 * | 10/2002 | Wang | 211/60.1 |
| 2010/0193453 A1 * | 8/2010 | Dunn et al. | 211/60.1 |

* cited by examiner

DENTAL BUR STORAGE DEVICE

INTRODUCTION

This invention relates to the dental industry. In particular, the invention relates to a dental bur storage device for use by dentists.

Throughout the following specification, the terms "bur" or "dental bur" shall be understood to encompass any type of drill bit that is attached to a dental handpiece, commonly called a dental drill, and used in dental, medical or veterinary procedures. In particular, it shall encompass both friction-grip drill bits and latch-grip drill bits.

A large portion of dental work involves the use of a drill to remove decayed portions of teeth and/or reshaping of dental tissues, enamel, dentine or bone. A dental drill consists of a handpiece to which a number of different dental burs are releasably attached. Various different types of dental burs are used by a dentist in order to carry out different types of dental procedures. For example, a round headed bur is typically used in cavity preparations. A pear shape headed bur is used for splitting roots of small teeth, and, a crosscut tapered fissure headed bur is used for sectioning multi-rooted teeth and reducing crown height. There are also finishing burs which are used for finishing work which is applied to dental procedures.

The dental burs generally consist of a head attached by a neck to a bur shank. The head contains blades or abrasive surfaces which perform the drilling into the patient's teeth. As mentioned hereinbefore, different types of blade design, surface treatment and shapes of head will provide different results with varied levels of accuracy and contour and therefore, different dental burs are used for carrying out different procedures which necessitate coarse-levels of dental work or fine-levels of dental work. The bur shanks are used to attach the dental burs to the handpiece. The shanks form the connection between the dental handpiece and the bur head and pass the rotational power from the handpiece to the bur head. As the bur head is rotated at high speeds for certain types of dental procedures, the connection must be very secure and the shank is constructed so as to provide as secure a connection point as possible at the free end of the shank, which opposes the bur head end of the bur shank, and is connected to the handpiece.

There are predominately two different types of dental burs differentiated by the manner in which the connection between the dental bur and the dental handpiece is achieved: friction-grip dental burs and latch-grip dental burs. These two different types of dental burs have differently shaped shanks, having different connection points and in some cases different diameter sizes. The latch grip burs comprise a latching mechanism, such as a mushroom-shaped nub, to clip into a part of the handpiece. The friction grip dental bur has a straight shank which is gripped by a releasable clamp that forms part of the dental handpiece.

It is not unusual for dentists to use both types of dental burs in order to have a full range of different dental burs and drilling options available to them to carry out various dental procedures. Different manufacturer models and bur types suit different dentists as the working practice of the dentist varies and different manufacturer types and bur types will suit different working practices. Also dentists will feel more comfortable working with certain types of burs and manufacturer types. Therefore, it is not uncommon for a dentist to use several different bur types from several different manufacturers during a single dental procedure in order to provide the best dental care to a patient.

In order to maximise the efficiency during a dental procedure, it is common for dentists to lay out all of the equipment including the different dental burs that they will require to carry out the procedure next to the dental chair prior to commencing the procedure. In this manner, at no time during the dental procedure will the dentist have to spend time looking for a particular piece of equipment while the patient is waiting for them to finish the procedure. As patients must keep their mouth open for long periods of time during dental procedures, more often than not with pieces of dental equipment therein, any delay during the procedure will require the patient to spend more time with their mouth open which will increase the discomfort felt by the patient during the dental procedure.

The various different types of dental burs may be laid out on a piece of cloth or any planar surface close to the dentist, or, may be kept in a storage device called usually a dental bur block.

There are hygiene issues with these approaches as the surface, the cloth or the dental bur block must be sterilised to ensure that the dental burs do not become dirty or unhygienic.

The dental bur block is usually made by a manufacturer of dental burs as an ancillary product, and typically comprises a plurality of cylindrically shaped holes which are specifically dimensioned for each type and size of dental bur. The dental bur block supplied by a particular manufacturer comprises holes that are designed to only receive shanks of one particular diameter size, from that particular manufacturer. It is important to note that as the hole is designed for one type of dental bur only, namely a friction-grip dental bur or a latch-grip dental bur, the holes cannot accommodate both types of dental burs. Therefore, if a dentist wishes to have a large range of different types of dental burs available to them during a dental procedure, a plurality of different dental bur blocks from different manufacturers must be arranged next to one another to present a lot of different types of different dental burs from the different manufacturers to the dentist.

Moreover, a further disadvantage of the currently available manufacturer made dental bur blocks is that dentists cannot arrange the dental burs into their preferred workflow layout. The manufacturer made dental bur blocks have specifically designed holes of certain sizes already laid out on the bur block to fit the different types of dental burs supplied by the manufacturer. Large headed burs, having relatively large shank diameters, require large holes, and smaller headed burs which are used for finer dental work will normally have smaller shank diameters and will only fit snugly in a hole which has a smaller size. Usually the layout of the holes on a manufacturer's dental bur block presents the dental burs in an ascending order of size, with small holes at one end and larger holes at an opposing end of the manufacturer made dental bur block. Consequently, a dentist cannot re-arrange the dental burs into a series of adjacent dental burs according to the workflow required for a particular dental procedure as the manufacturer made dental bur blocks do not allow for this.

Even with just one manufacturer made dental bur block, it is still awkward for a dentist to quickly identify and locate the bur they need for the next portion of the dental procedure. The dentist must be sure to remove the correct dental bur from the manufacturer made dental bur block as very similar types of burs are typically found beside one another in the prearranged layout on the manufacturer made dental bur block. It is easy for the dentist to make an error by selecting a dental bur which is slightly bigger, or slightly smaller than the dental bur which they intended to use as the larger/smaller dental bur was located next to the desired dental bur on the manufacturer made dental bur block. As can be easily imagined, this issue slows down the dental procedure which may increase the discomfort for the patient, decreased the efficiency of the dental practice and may potentially cause the dentist to make an error in selecting the incorrect dental bur for the dental procedure.

As previously mentioned, if the dentist wishes to use a number of different burs from different manufacturers, the problem is compounded as the number of manufacturer specific dental bur blocks required by the dentist becomes greater. Thus, it becomes even more cumbersome for the dentist to navigate all of the different dental bur blocks and remember which manufacturer made dental bur block holds which type of dental bur. It will consequently take longer for the dentist to navigate the plurality of different blocks, and the patient will feel more discomfort as the dental procedure will inevitably last longer.

Furthermore, the manufacturer made dental bur blocks do not allow a dentist to easily label the dental bur block with their own labels. It is known that labelling a dental bur block can greatly assist a dentist to quickly find the correct dental bur which is required for the subsequent action during the dental procedure. In some cases, a dentist will be carrying out a procedure without the help of a dentist's assistant and may have to hold some dental equipment in place inside of a patient's mouth whilst reaching over to a chair-side table which has the dental bur lock on it. Often times, this chair-side table is behind the dentist added is awkward for the dentist to easily see the dental burs on the dental bur block. Therefore, it has been found that clear labelling is very important and can greatly assist a dentist in carrying out a dental procedure.

At present, whilst some of the manufacturer made dental bur blocks comprise size markings adjacent particular holes, the markings are permanently part of the dental bur block and cannot be removed, alter or replaced. Therefore, a dentist cannot easily place of their own labels on any of the currently available dental bur blocks. As the dental bur blocks must be sterilised regularly, it is not acceptable to use common labelling methods such as stickers which pose hygienic risks to the dental bur block.

In order for a dental practice to work efficiently, a dentist should preferably move from one patient to the next as quickly as possible. In order to achieve as high efficiency as possible, the burs required for each procedure should be laid out in advance of the patient's entering the dental surgery. Preferably, a plurality of different dental bur blocks should be pre-loaded with the dental burs required for each of the dental procedures that will be carried out on all of the patients before that working day. Even if the dental practice does not have enough dental equipment to facilitate pre-loading a plurality of dental bur blocks for the entire working day, at least to dental bur blocks could be pre-loaded with the dental burs wired for the dental procedure is to be carried out on the next two patients. In this scenario, the plurality of dental bur blocks will be moved about the dental practice with the dental burs inserted into them. It is very important that the holes in the dental bur blocks which are used to receive and retain the dental burs do so in a tight fitting and secure manner.

It is a goal of the present invention to provide an apparatus/method that overcomes many of the above mentioned problems.

SUMMARY OF THE INVENTION

The present invention is directed towards a dental bur storage device having a plurality of dental bur receiving holes capable of retaining a plurality of different dental bur types having different shank diameters, wherein, each of the plurality of dental bur receiving holes is tapered to allow a retaining fit to be established with any one of the plurality of different dental bur types having different shank diameters.

The advantage of using a receiving hole that has a tapered form is that different types of dental burs having different sized shank diameters may be retained by the receiving holes in the dental bur storage device. This allows a wide range of different brands and different types of dental burs to be accommodated on one single dental bur storage device, or dental bur block, which greatly simplifies the process of selecting a dental bur for a dentist, particularly during a dental treatment.

As the receiving hole is tapered, bur shanks of varying dimensions will be received to different depths within the receiving hole to a point where the receiving hole tapers to a diameter substantially equal to the diameter of the shank of the dental bur being received. In this manner, the dental burs regardless of the manufacturer type, size of the bur and size of the shank down matter will be held securely within the dental bur storage device. This allows the dental bur storage device to be moved around the dental practice without concern for one of the dental burs inserted into the dental bur storage device becoming dislodged and falling out of the dental bur storage device. Thus, using this type of receiving hole, positive retention of a dental bur may be achieved when the dental bur storage device is handled roughly or inverted.

All the dental burs are easily visible and locatable by a dentist at a glance as the dental burs may be arranged in the dental bur storage device according to the workflow pattern which best suits the dental procedure and the dentist's working practices preferences. The dentist is not confined to arranging the dental burs on the dental bur storage device according to a pre-arranged bur receiving hole layout which is decided by a manufacturer rather than the dentist themselves.

In a further embodiment, the plurality of dental bur receiving holes are each tapered along their longitudinal axis.

In a further embodiment, each of the dental bur receiving holes is substantially frusto-conical in shape. This is advantageous as it allows for simpler placement of the dental bur into the dental bur receiving hole. This is particularly important for dentists who do not wish to be distracted during a dental procedure and would prefer to be able to place a dental bur into a bur receiving hole without having to pay undue attention to the act of placing the dental bur into the bur receiving hole.

In a further embodiment, each of the dental bur receiving holes is a parabolic cone.

In a further embodiment, the parabolic cone comprises curved sides.

The advantage of providing curved sides is that the rate at which the bur receiving hole tapers will be variable. Initially, adjacent the inlet of the bur receiving hole, the diameter of the hole can be made to be relatively wide to facilitate a quick and easy placement of a shank of a dental bur into the dental bur receiving hole. Thereafter, during a first portion of length of the hole, the inner diameter of the bur receiving hole decreases relatively quickly due to the curved, tapered nature of the bur receiving hole so to guide the shank of the dental bur towards the centre of the hole. During a subsequent portion of length of the bur receiving hole, the rate at which the bur receiving hole tapers is varied such that the hole tapers at a slower rate. This allows the bur receiving hole to provide more stability to the part of the bur shank inserted into this subsequent portion of length of the bur receiving hole.

In a further embodiment, each dental bur receiving hole comprises a plurality of inwardly extending shank-stabilising protrusions.

The inwardly extending shank-stabilising protrusions assist with retaining a shank of a dental bur which has a relatively large diameter. This is due to the fact that a shank having a relatively large diameter will not travel down much of the receiving hole as the relatively large diameter of the shank will prevent this from occurring. However, the radially inwardly extending shank-stabilising protrusions will assist with stabilising the dental bur even if the dental bur cannot travel very far down within the dental bur receiving hole due to the relatively large diameter of the shank.

The protrusions may preferably be constructed from a compressible material so as to minimise their impact on allowing the easy insertion of a shank into the receiving hole.

In a further embodiment, the plurality of shank-stabilising protrusions extend radially inwards towards a central longitudinal axis of each dental bur receiving hole.

In a further embodiment, the plurality of inwardly extending shank-stabilising protrusions are located substantially adjacent an inlet of the dental bur receiving hole.

In a further embodiment, the plurality of radially inwardly extending shank-stabilising protrusions are tear-shaped nodules.

In a further embodiment, each dental bur receiving hole comprises a bevelled inlet edge. The bevelled inlet edge will further facilitate the easy insertion of a dental bur into the receiving hole. In yet a further embodiment, each of the dental bur receiving holes comprises a chamfered inlet.

In a further embodiment, each of the dental bur receiving holes is a through hole. By producing the dental bur storage device with through holes, this will allow the dental bur storage device to be thoroughly washed and sterilised and drained prior to re-use. Such hygienic issues are of extreme importance in dental practices.

In a further embodiment, the plurality of dental bur receiving holes are arranged in rows and columns, and, the dental bur storage device further comprises one or more label mounts adjacent the rows and columns to allow a dentist to identify the different dental bur types retained in the plurality of dental bur receiving holes.

The advantage of providing label mounts is that a dentist may organise the dental bur storage device according to their own liking and their preferred workflow and working practice and preference. This will facilitate a faster retrieval of the correct dental bur by the dentist, and thus shorten the overall dental procedure and maximise the practice efficiency. Moreover, the dentist will not have to attempt to locate the correct bur during a dental procedure which may cause further discomfort to a patient.

The labelling system also allows for an easy and quick stock check to be performed, and the labelling can be used to help a dentist's assistant in re-ordering dental burs for the dentist. In particular, if a dentist places a number of dental burs along a first row of dental bur receiving holes in the dental bur storage device, and a second, back-up set of dental burs are placed in a second row of dental bur receiving holes which sit behind the first row of dental bur receiving holes in the dental bur storage device, then the dentist's assistant can quickly and simply assess the working condition of a dental bur by comparing it to the dental bur in the second, back-up row. A stock control can be thus quickly carried out and replacement burs can be ordered as necessary.

In a further embodiment, the dental bur storage device comprises a detachable label placeholder.

In a further embodiment, the dental bur storage device comprises one or more frangible lines of weakness so as to allow the dental bur storage device to be split into two or more smaller dental bur storage units.

In a further embodiment, the one or more frangible lines of weakness comprise a notch running partially through the dental bur storage device. In yet a further embodiment, the notch is a V-shaped notch.

In a further embodiment, at least one of the one or more frangible lines of weakness runs along a central axis of the dental bur storage device so as to allow the storage device to be split into two substantially equally sized dental bur storage devices.

In a further embodiment, the dental bur storage device comprises one or more connection points so as to allow two or more smaller dental bur storage units to be joined to form a larger dental bur storage device. The connection points may be preferably male and female connectors, snap-together buttons and sockets, pin and complementary slot systems and the like.

In a further embodiment, the dental bur storage device further comprises one or more fixture engaging mounts and/or a plurality of surface engaging studs.

In a further embodiment, the one or more fixture engaging mounts and/or a plurality of surface engaging studs are located on a back face of the dental bur storage device.

In a further embodiment, the one or more fixture engaging mounts are keyhole slots.

In a further embodiment, the detachable label placeholder comprises a transparent lid.

In a further embodiment, the dental bur storage device is constructed of an autoclavable material. In a further embodiment, the dental bur storage device is constructed of silicone.

In a further embodiment, the dental bur storage device comprises a substantially planar display face.

In a further embodiment, the plurality of dental bur receiving holes are arranged in rows and columns on the dental bur storage device.

The present invention is further directed towards a dental bur storage device having a plurality of dental bur receiving holes for receiving and retaining a plurality of different dental burs used in dental treatments, wherein, the different dental burs are different types of dental burs having different shank diameters, and, each of the plurality of dental bur receiving holes is tapered along its longitudinal axis to allow a retaining fit to be established with any one of the plurality of different types of dental burs having different shank diameters.

DETAILED DESCRIPTION OF EMBODIMENTS

The invention will be more clearly understood by the following description of some embodiments thereof, given by way of example only with reference to the accompanying drawings, in which.

Figure 1:
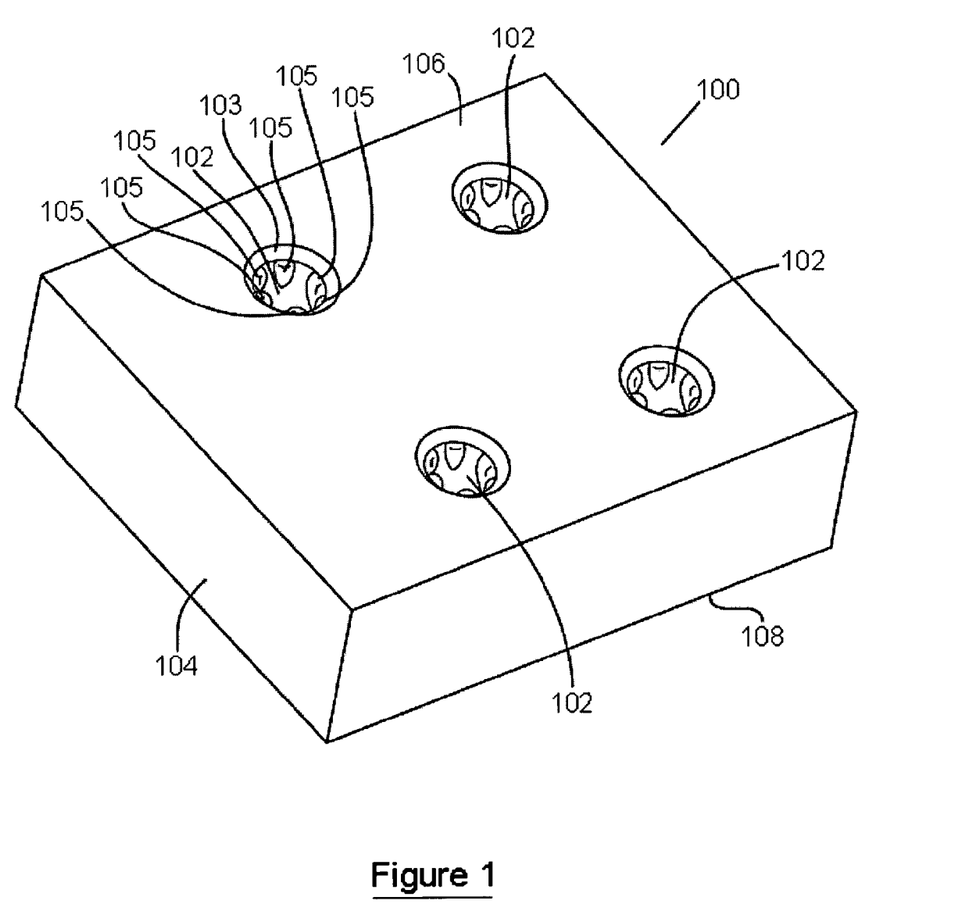
FIG. 1 is a perspective view of a dental bur storage device in accordance with the present invention.
Figure 2:
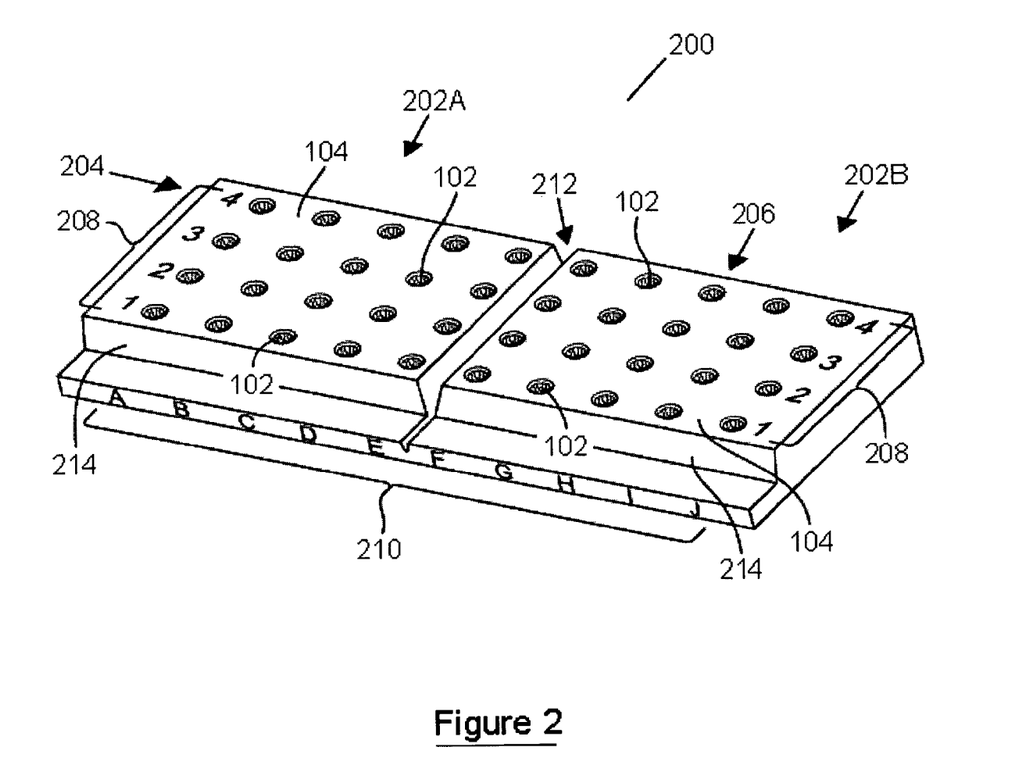
FIG. 2 is a perspective view of a dental bur storage device in accordance with a further embodiment of the present invention.
Figure 3:
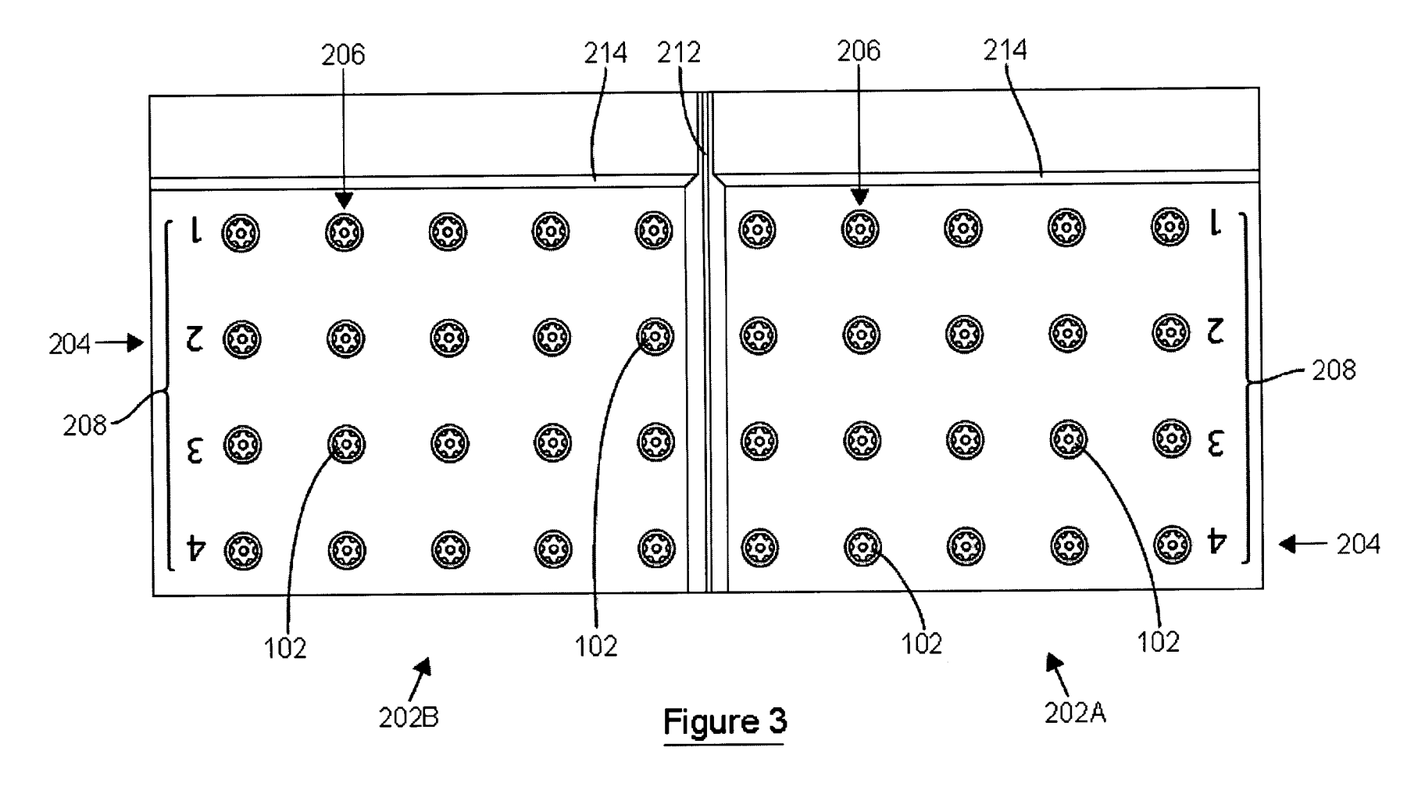
FIG. 3 is a plan view of the dental bur storage device of FIG. 2.
Figure 4:
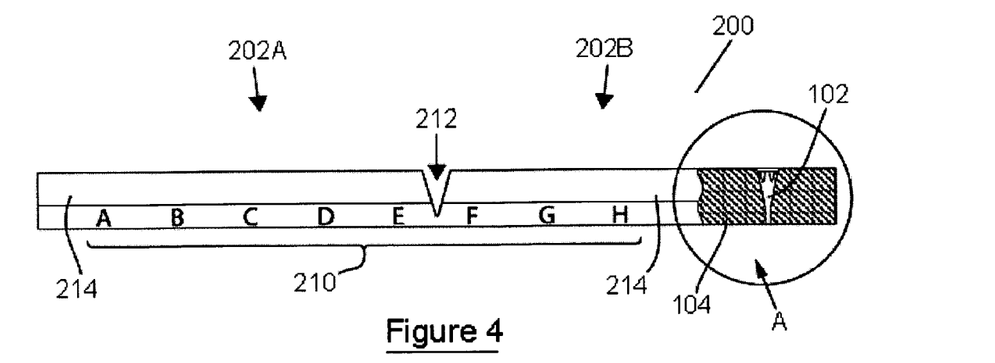
FIG. 4 is a partially sectioned elevational view of the dental bur storage device of FIG. 2.

Referring to the drawings and initially to FIG. 1 thereof, there is provided a dental bur storage device according to the present invention indicated generally by the reference numeral 100. The dental bur storage device 100 comprises a plurality of spaced-apart dental bur receiving holes 102. The plurality of dental bur receiving holes 102 pass through a block 104 of autoclavable material, such as silicone. The dental bur storage device 100 comprises a display face 106 and a back face 108. Each of the bur receiving holes 102 tapers inwardly along a longitudinal axis of the bur receiving holes 102, resulting in a narrower outlet of the bur receiving hole 102 on the back face 108 of the dental bur storage device 100 in comparison to an inlet of the bur receiving hole 102 on the display face 106 of the dental bur storage device 100.

Each receiving hole 102 comprises a bevelled inlet portion 103 on the display face 106 side of the dental bur storage device 100, and, a plurality of radially inwardly extending dental bur-stabilising protrusions 105 which are located substantially adjacent the bevelled inlet portion 103 of the receiving holes 102.

In use, a shank (not shown) of a dental bur (not shown) is inserted into one of the receiving holes 102. The bevelled inlet portion 103 is dimensioned to accommodate different types of dental burs having different shank diameters and direct the shank of the dental bur towards the central longitudinal axis of the bur receiving hole 102.

As the shank of the dental bur is pushed down into the bur receiving hole 102, the tapered inner diameter of the receiving hole 102 will guide the shank towards the central longitudinal axis of the bur receiving hole 102. At a particular point, when the diameter of the lowermost portion of the shank is substantially equal to the diameter of the bur receiving hole 102 at the point in the bur receiving hole 102 which is in contact with the lowermost portion of the shank, the diameter of the shank will prevent the shank from travelling any further down inside the bur receiving hole 102. The tapered shape of the receiving hole 102, with the assistance of the plurality of radially inwardly extending dental bur-stabilising protrusions 105, will retain the dental bur in the receiving hole 102.

With reference to FIGS. 2 to 5, wherein like parts previously described have been assigned the same reference numerals, there is provided a further dental bur storage device according to a second embodiment of the invention which is indicated generally by the reference numeral 200. The dental bur storage device 200 comprises two joined half-sections 200A, 200B which are dental bur storage units. Each half-section dental bur storage unit 200A, 200B comprises a plurality of receiving holes 102 set into an autoclavable block 104.

The plurality of dental bur receiving holes 102 are arranged in four rows 204 of five columns 206 on each of the half-section dental bur storage units 200A, 200B.

A set of numerical labels 208 are provided adjacent each of the four rows 204 on the dental bur storage device 200, and a set of alphabetical labels 210 are also provided substantially adjacent and associated with each of the ten columns 206 on the dental bur storage device 200.

A V-shaped notch 212 is provided along a central axis of the dental bur storage device 200 to allow a user to break the dental bur storage device 200 into two separate dental bur storage units formed from the two half-section dental bur storage units 200A, 200B. An angled face 214 is provided along one side of the dental bur storage device 200. Information, such as labelling may be advantageously placed on this angled face 214 so as to be easily visible to a dentist or user.

Figure 5:
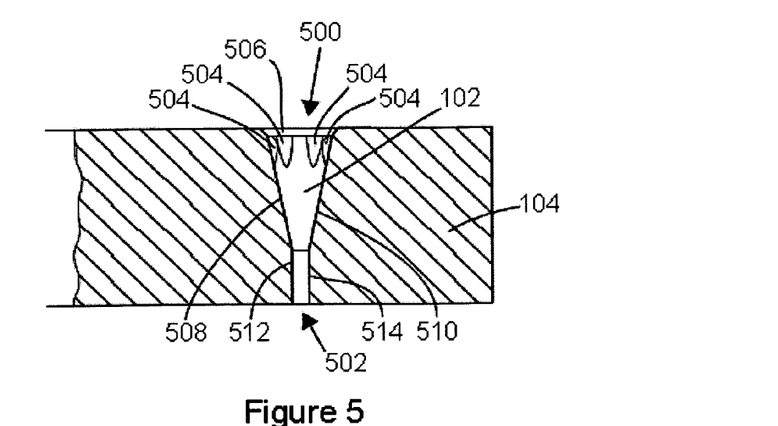
FIG. 5 is an enlarged detail sectional view showing the encircled portion A of FIG. 4.

Referring to FIG. 5 in particular, each receiving hole 102 passes through the autoclavable block of material 104 and comprises an inlet 500 and an outlet 502, thus forming a through hole. A plurality of radially inwardly extending dental bur-stabilising protrusions, which are in the form of bur-stabilising tear-shaped nodules 504, are provided adjacent the inlet 500. The bur-stabilising tear-shaped nodules 504 are used to assist with providing a further stability and retention of a dental bur (not shown) when it is inserted into the bur receiving hole 102. The inlet portion 506 of each bur receiving hole 102 is bevelled or chamfered to help guide a shank (not shown) of a dental bur (not shown) towards a central longitudinal axis of the bur receiving hole 102 and facilitate easy insertion of the shank into the bur receiving hole 102.

The bur receiving hole 102 is tapered from its inlet 500 towards its outlet 502. The receiving hole 102 is tapered to form a frusto-conical shape so that the rate of tapering is constant along the longitudinal length of the receiving hole 102.

Therefore, when viewed in cross-section, the receiving hole 102 in FIG. 5 comprises an upper bevelled inlet portion 506, an intermediate tapered portion having straight sides 508, 510 which taper from the inlet 500 towards the outlet 502, and, a lower cylindrical-shaped portion having sides 512, 514 that are substantially parallel to one another when viewed in cross-section and are provided along a portion of the longitudinal axis of the receiving hole 102 adjacent the outlet 502.

Figure 6:
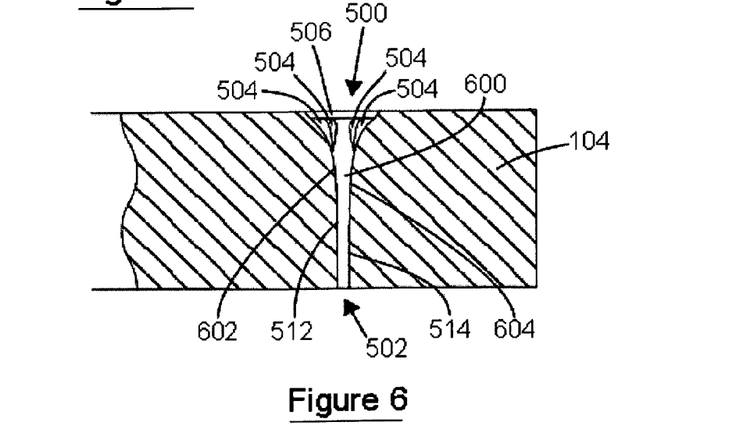
FIG. 6 is a detail view of a receiving hole in a dental bur storage device in accordance with a further embodiment of the present invention.

Referring to FIG. 6, wherein like parts previously described have been assigned the same reference numerals, there is provided a third embodiment of the present invention, wherein the tapered form of the bur receiving hole 102 is altered. Each bur receiving hole 102 passes through the autoclavable block of material 104 as before and also comprises an inlet 500 and an outlet 502, thus forming a through hole which is useful for thorough sterilisation of the bur storage device 100, 200. The plurality of bur-stabilising tear-shaped nodules 504 are again provided adjacent the inlet 500. The inlet portion 506 of each receiving hole 102 is bevelled to guide a shank (not shown) of a dental bur (not shown) for easy insertion of the shank into the receiving hole 102.

The receiving hole 102 is tapered from its inlet 500 towards its outlet 502. The receiving hole 102 is tapered in the form of a parabolic sided cone, such that the side surface of the parabolic sided cone is curved with respect to a central longitudinal axis of the parabolic sided cone. Thus, when viewed in cross-section, the sides of the parabolic sided cone are curved so that the rate of tapering changes along the longitudinal length of the receiving holes 102.

Therefore, when viewed in cross-section, the receiving hole 600 in FIG. 6 comprises an upper bevelled inlet portion 506, an intermediate tapered portion having curved sides 602, 604 which taper from the inlet 500 towards the outlet 502, and, a lower cylindrical-shaped portion having sides 512, 514 that are substantially parallel to one another when viewed in cross-section and are provided along a portion of the longitudinal axis of the receiving hole 102 adjacent the outlet 502.

With reference to FIGS. 7 to 12, wherein like parts previously described have been assigned the same reference numerals, there is provided a further dental bur storage device according to a fourth embodiment of the invention which is indicated generally by the reference numeral 700.

Figure 7:
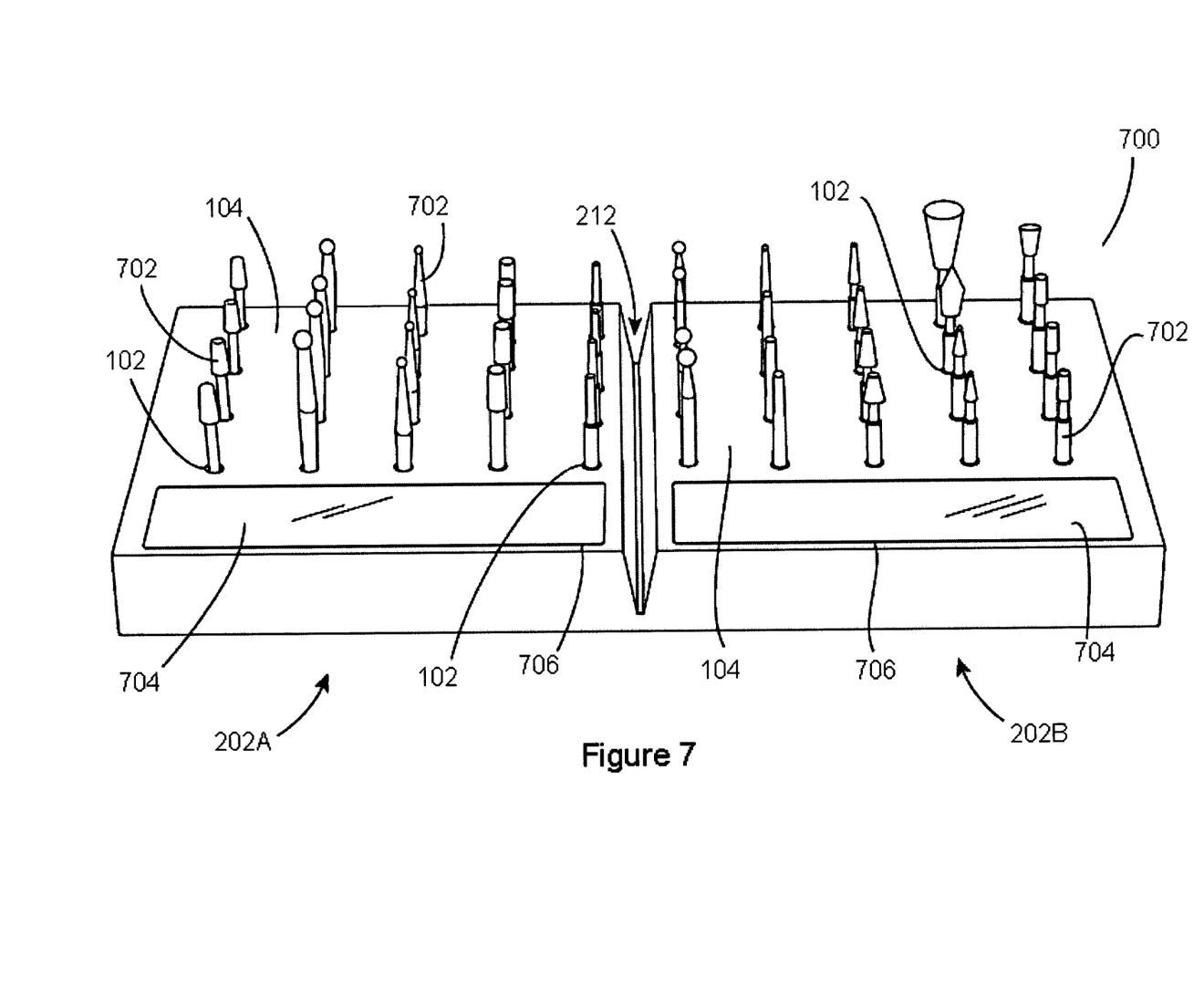
FIG. 7 is a perspective view of a dental bur storage device in accordance with a further embodiment of the present invention.
Figure 8:
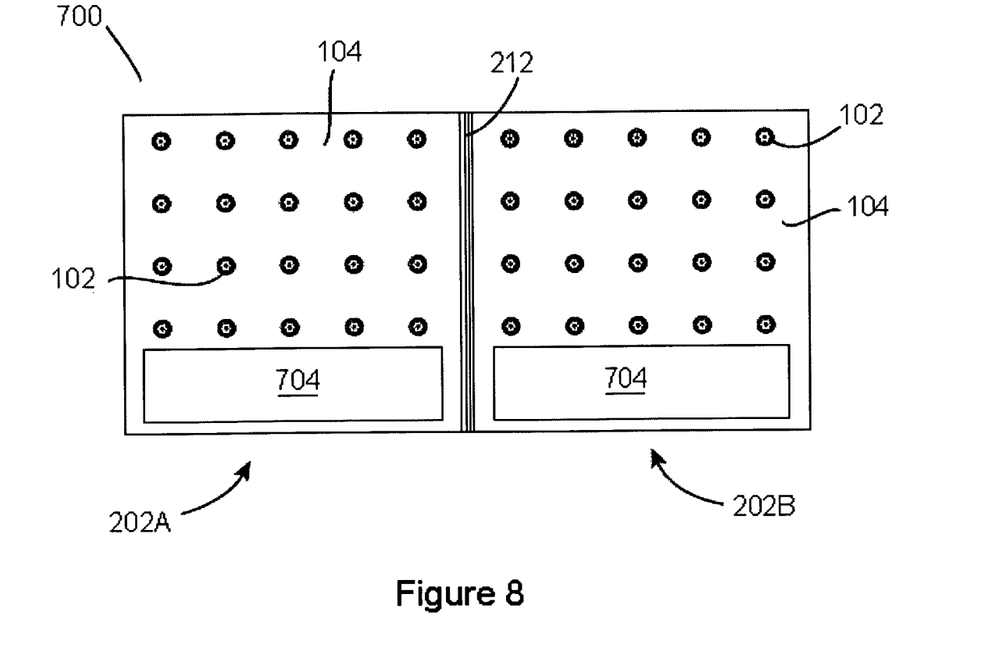
FIG. 8 is a plan view of the dental bur storage device of FIG. 7 with label placeholders in situ.

The bur storage device 700 comprises a plurality of bur receiving holes 102 which are shown to receive and retain a plurality of dental burs 702. As can be seen, in some cases, back-up dental burs 702 are provided in bur receiving holes behind a foremost dental bur 702 to allow a dentist to quickly have access to a back up dental bur 702 should the original dental bur fail to operate correctly, and, this arrangement also allow a dentist's assistant to perform a quick stock check and quality assurance check by scanning their eyes over the bur storage device 700.

The dental bur storage device 700 comprises two joined dental bur storage units 200A, 200B which are separated and connected by a frangible line of weakness. The frangible line of weakness is comprised of a V-shaped notch 212 that is provided along a central axis of the dental bur storage device 700. A dentist can break the dental bur storage device 700 into two separate dental bur storage units 200A, 200B.

Each dental bur storage unit 200A, 200B comprises a plurality of receiving holes 102, which in the present embodiment is four rows of five columns, which are set into the autoclavable block of material 104.

Figure 9:
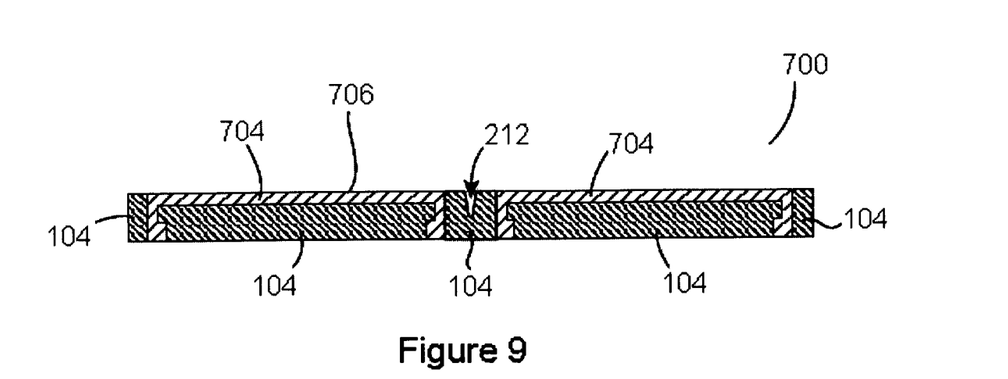
FIG. 9 is a sectioned plan view of the dental bur storage device of FIG. 7 with label placeholders in situ.
Figure 10:
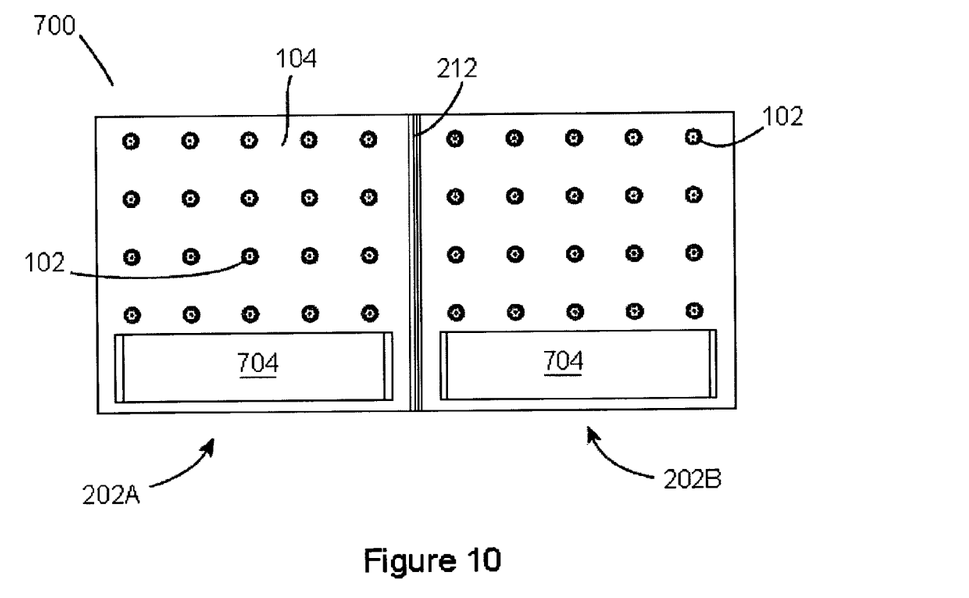
FIG. 10 is a plan view of the dental bur storage device of FIG. 7 without the label placeholders in situ.
Figure 11:
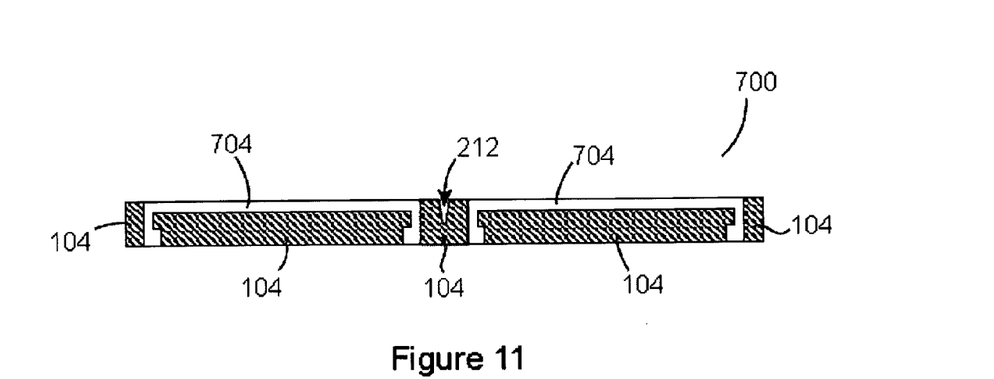
FIG. 11 is a sectioned plan view of the dental bur storage device of FIG. 7 without the label placeholders in situ; and, FIG. 12 is a perspective view of the label placeholder used in conjunction with the dental bur storage device of FIG. 7.
Figure 12:
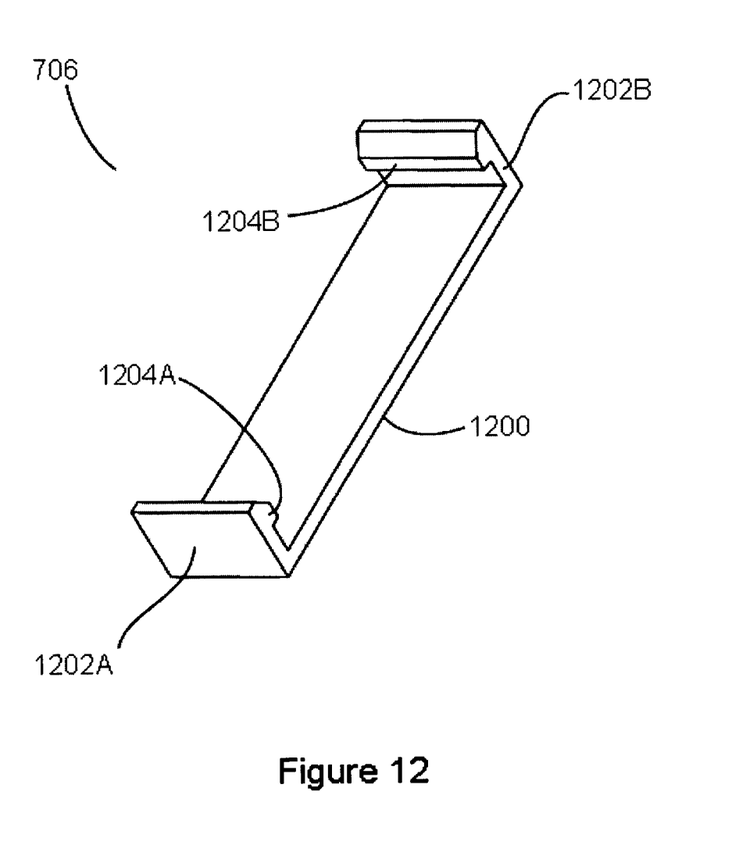

The dental bur storage device 700 further comprises labelling placeholders 704 on each of the dental bur storage units 200A, 200B in front of the foremost row of bur receiving holes 102. The labelling placeholders 704 comprise a detachable protective lid 706 which snap fits into a complementary receiving slot that is manufactured within the dental bur receiving device 700. With particular reference to FIGS. 9 and 11, the detachable protective lid 706 is shown in situ in the labelling placeholder slot and absent from the labelling placeholder slot respectively. With reference to FIG. 12, the detachable protective lid 706 comprises a covering face 1200 with depending legs 1202A, 1202B which terminate with retaining clips 1204A, 1204B. It will be appreciated that the dental bur storage device 700 may preferably comprises labelling placeholder slots which are through and through to allow thorough sterilisation to take place.

In a further embodiment (not shown), it will be appreciated that the bur-stabilising tear-shaped nodules 504 may be made of an easily compressible material as not to hinder the insertion of a shank of a dental bur into the receiving hole 102. In further embodiment, the bur-stabilising tear-shaped nodules 504 are made of the same material as the autoclavable block 104.

Whilst two of the above-mentioned embodiments have been shown to comprise ten columns of four rows, and one of the embodiments has been shown to comprise two rows of two columns, it will be readily appreciated that any combination of rows and columns may be used. Indeed, the bur receiving holes do not have to be grouped into rows and columns, but rather maybe arranged in any pattern so as to form a set of holes that are easy to navigate and/or label by a dentist. In a preferred embodiment, the dental bur storage device comprises a stepped or sloped display face to present the dental burs to the dentist in a more accessible manner.

The receiving holes 102 may alternatively comprise a stepped inner diameter which is reduced in a step-like manner along the depth of the bur receiving hole, so as to allow different shanks having different diameters to be received and retained within the receiving hole 102. Alternatively, the receiving hole 102 may comprise a deformable ring of material within the receiving hole, whereby, the deformable ring of material can be compressed depending on the diameter of the shank which is being inserted into the hole.

In the specification the terms "comprise, comprises, comprised and comprising" or any variation thereof and the terms "include, includes, included and including" or any variation thereof are considered to be totally interchangeable and they should all be afforded the widest possible interpretation and vice versa.

The invention is not limited to the embodiments hereinbefore described which may be varied in both construction and detail.

The invention claimed is:

1. A dental bur storage device comprising:
   a plurality of dental bur receiving holes capable of retaining a plurality of different dental bur types having different shank diameters,
   wherein, each of the plurality of dental bur receiving holes is tapered in a frusto-conical configuration such that tapered side walls of the receiving holes are configured to engage the differing shank diameters, causing a retaining fit to be established with any one of the plurality of different dental bur types having different shank diameters, and
   wherein the tapered side walls of each of the plurality of dental bur receiving holes further comprises a plurality of inwardly extending shank-stabilizing protrusions.

2. The dental bur storage device as claimed in claim 1, wherein the plurality of dental bur receiving holes are each tapered along their longitudinal axis.

3. The dental bur storage device as claimed in claim 1, wherein the plurality of shank-stabilising protrusions extend radially inwards towards a central longitudinal axis of each dental bur receiving hole.

4. The dental bur storage device as claimed in claim 1, wherein the plurality of inwardly extending shank-stabilising protrusions are located substantially adjacent an inlet of the dental bur receiving hole.

5. The dental bur storage device as claimed in claim 1, wherein the plurality of radially inwardly extending shank-stabilising protrusions are tear-shaped nodules.

6. The dental bur storage device as claimed in claim 1, wherein each dental bur receiving hole comprises a bevelled inlet edge.

7. The dental bur storage device as claimed in claim 1, wherein each of the dental bur receiving holes is a through hole.

8. The dental bur storage device as claimed in claim 1, wherein the plurality of dental bur receiving holes are arranged in rows and columns, and, the dental bur storage device further comprises one or more label mounts adjacent the rows and columns to allow a dentist to identify the different dental bur types retained in the plurality of dental bur receiving holes.

9. The dental bur storage device as claimed in claim 1, wherein the dental bur storage device comprises one or more frangible lines of weakness so as to allow the dental bur storage device to be split into two or more smaller dental bur storage units.

10. The dental bur storage device as claimed in claim 9, wherein the one or more frangible lines of weakness comprise a notch running partially through the dental bur storage device.

11. The dental bur storage device as claimed in claim 1, wherein the dental bur storage device is constructed of an autoclavable material.

\* \* \* \* \*